(12) United States Patent
Brown, III

(10) Patent No.: US 6,168,616 B1
(45) Date of Patent: Jan. 2, 2001

(54) MANUALLY EXPANDABLE STENT

(75) Inventor: Charles L. Brown, III, Atlanta, GA (US)

(73) Assignee: Global Vascular Concepts, Atlanta, GA (US)

( * ) Notice: Under 35 U.S.C. 154(b), the term of this patent shall be extended for 0 days.

(21) Appl. No.: 09/089,289

(22) Filed: Jun. 1, 1998

Related U.S. Application Data

(60) Provisional application No. 60/048,358, filed on Jun. 2, 1997.

(51) Int. Cl.$^7$ .............................. A61F 2/06; A61F 11/00; A61M 29/00
(52) U.S. Cl. ........................ 623/1.11; 606/198; 606/108
(58) Field of Search ...................... 623/1, 1.11; 606/198, 606/195, 191, 194, 200, 108

(56) References Cited

U.S. PATENT DOCUMENTS

| | | |
|---|---|---|
| 4,950,227 | 8/1990 | Savin et al. . |
| 5,041,126 | 8/1991 | Gianturco . |
| 5,108,416 | 4/1992 | Ryan et al. . |
| 5,158,548 | 10/1992 | Lau et al. . |
| 5,242,399 | 9/1993 | Lau et al. . |
| 5,344,426 | 9/1994 | Lau et al. . |
| 5,403,341 | 4/1995 | Solar . |
| 5,445,646 | 8/1995 | Euteneuer et al. . |
| 5,453,090 | 9/1995 | Martinez et al. . |
| 5,480,423 | 1/1996 | Ravenscroft et al. . |
| 5,487,730 * | 1/1996 | Marcadis et al. ................ 604/96 |
| 5,496,277 * | 3/1996 | Termin et al. ................. 604/104 |
| 5,507,768 | 4/1996 | Lau et al. . |
| 5,534,007 | 7/1996 | St. Germain et al. . |
| 5,549,635 | 8/1996 | Solar . |
| 5,556,414 | 9/1996 | Turi . |
| 5,569,295 | 10/1996 | Lam . |
| 5,571,135 | 11/1996 | Fraser et al. . |
| 5,643,278 | 7/1997 | Wijay . |
| 5,658,311 | 8/1997 | Baden . |
| 5,662,703 | 9/1997 | Yurek et al. . |
| 5,669,932 | 9/1997 | Fischell et al. . |
| 5,690,643 * | 11/1997 | Wijay ........................ 606/198 |
| 5,693,066 | 12/1997 | Rupp et al. . |
| 5,702,418 | 12/1997 | Ravenscroft . |
| 5,702,419 | 12/1997 | Berry et al. . |
| 5,713,907 * | 2/1998 | Hogendijk et al. ............ 606/108 |
| 5,735,859 | 4/1998 | Fischell et al. . |
| 5,741,270 * | 4/1998 | Hansen et al. ................ 606/108 |
| 5,766,203 | 6/1998 | Imran et al. . |
| 5,772,669 | 6/1998 | Vrba . |
| 5,776,141 | 7/1998 | Klein et al. . |
| 5,776,142 | 7/1998 | Gunderson . |
| 5,782,855 | 7/1998 | Lau et al. . |
| 5,792,172 | 8/1998 | Fischell et al. . |
| 5,807,398 | 9/1998 | Shaknovich . |
| 5,810,874 * | 9/1998 | Lefebvre ..................... 606/200 |
| 5,817,100 | 10/1998 | Igaki . |
| 5,817,102 | 10/1998 | Johnson et al. . |
| 5,843,090 | 12/1998 | Schuetz . |
| 5,855,565 * | 1/1999 | Bar-Cohen et al. ............ 604/104 |
| 5,871,538 * | 2/1999 | Dereume ..................... 623/1 |
| 5,913,871 | 6/1999 | Werneth et al. . |
| 5,944,726 | 8/1999 | Blaeser et al. . |
| 5,951,569 | 9/1999 | Tuckey et al. . |
| 5,968,069 | 10/1999 | Dusbabek et al. . |
| 5,980,530 | 11/1999 | Willard et al. . |
| 5,989,280 | 11/1999 | Euteneuer et al. . |

* cited by examiner

Primary Examiner—V. Millin
Assistant Examiner—Alvin Stewart
(74) Attorney, Agent, or Firm—Sutherland Asbill & Brennan LLP

(57) ABSTRACT

A stent delivery system having a stent the girth of which expands upon longitudinal compression, a pair of telescoping tubes where the inner tube has a greater length than the outer tube, and the stent surrounds the inner tube, a distal deployment strut fixedly connected at one end to the inner tube, and at the other end non-fixedly connected to the stent, a proximal deployment strut fixedly connected at one end to the outer tube, and at the other end non-fixedly connected to the stent, and an anchoring barb at the distal end of the stent.

6 Claims, 7 Drawing Sheets

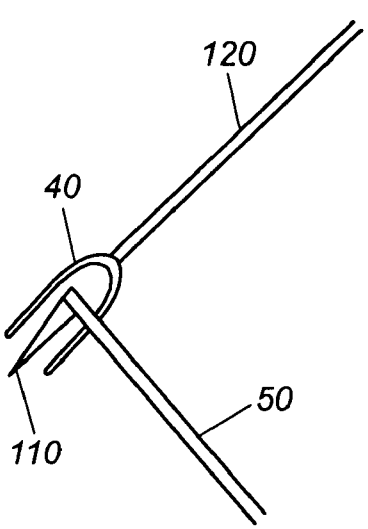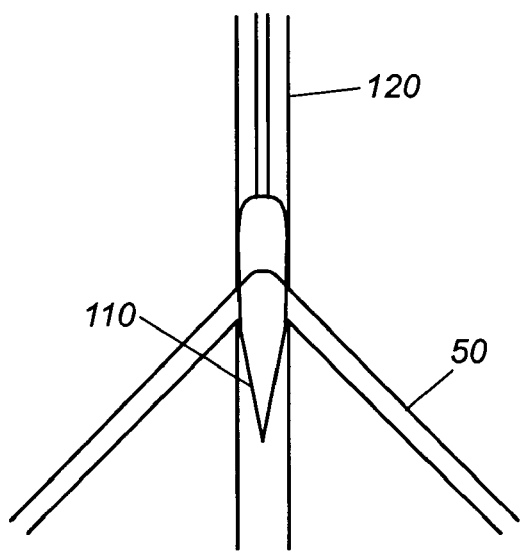
*Fig. 5a*  *Fig. 5b*
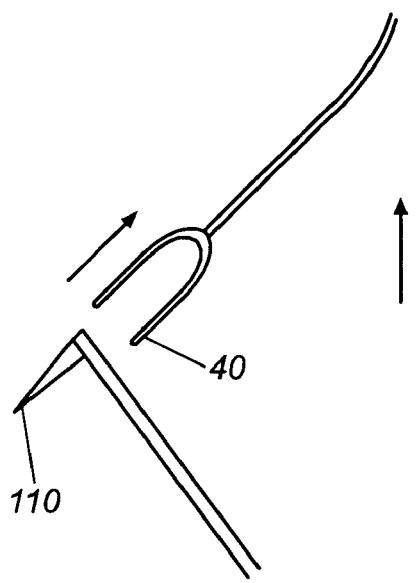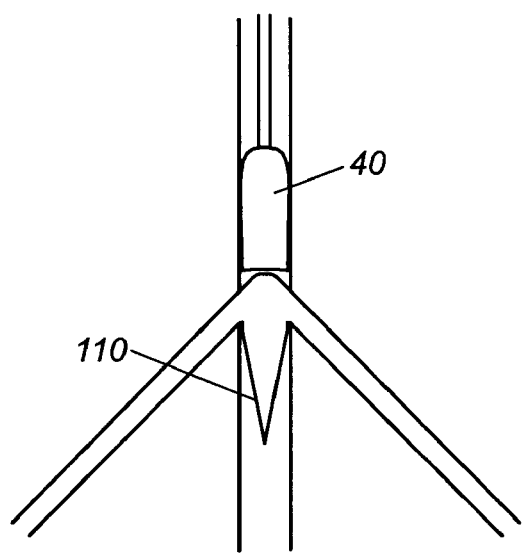
*Fig. 6a*  *Fig. 6b*

MANUALLY EXPANDABLE STENT

CROSS-REFERENCE TO RELATED APPLICATIONS

This application claims priority to U.S. Provisional Patent Application Ser. No. 60/048,358 filed Jun. 2, 1997.

FIELD OF THE INVENTION

The present invention is in the field of surgical implements, more particularly in the field of stents.

BACKGROUND OF THE INVENTION

The present invention relates to cardiovascular stents which can be inserted into a body lumen. More particularly, the present invention relates to a removable cardiovascular stent designed to operate with an extraction catheter to enable easy retrieval of the implanted stent.

A stent is typically a tubular metallic or polymeric body, which is carried on a dilation catheter to a specific vascular location. In one cardiovascular application, a stent is mounted on a balloon catheter and positioned at the appropriate site within an artery. The balloon is thereafter deflated and removed, leaving the expanded stent in place in the artery. The stent may also be self or thermally expanding, thus not requiring a balloon for placement. The arterial wall is supported by the stent and prevented from collapsing.

SUMMARY OF THE INVENTION

The present invention is a stent delivery system comprising a stent the girth of which expands upon longitudinal compression, a pair of telescoping tubes where the inner tube has a greater length than the outer tube, and the stent surrounds the inner tube, a distal deployment strut fixedly connected at one end to the inner tube, and at the other end non-fixedly connected to the stent, a proximal deployment strut fixedly connected at one end to the outer tube, and at the other end non-fixedly connected to the stent, and an anchoring barb at the distal end of the stent.

Therefore, it is an object of the present invention to provide a stent which is manually expandable, rather than balloon-expandable or self-expandable.

It is a further object of the invention to provide a stent which can be placed accurately within a vessel.

It is a further object of the present invention to provide a stent which has no balloon present to occlude visualization of the vessel lumen during deployment.

BRIEF DESCRIPTION OF THE DRAWINGS

FIG. 5a is an expanded side view of the distal deployment strut of the current invention, showing its non-fixed attachment to the distal end of the stent, and the anchoring barb cradled within the U-shaped end of the strut.

FIG. 5b is an expanded top view of the distal deployment strut of the current invention, showing its non-fixed attachment to the distal end of the stent, and the anchoring barb cradled within the U-shaped end of the strut.

FIG. 6a is an expanded view of the distal deployment strut of the current invention, just as it releases from the distal end of the stent and the anchoring barb comes forth.

FIG. 6b is an expanded view of the distal deployment strut of the current invention, just as it releases from the distal end of the stent and the anchoring barb comes forth.

DETAILED DESCRIPTION OF THE INVENTION

The present invention is a stent delivery system comprising a stent the girth of which expands upon longitudinal compression, a pair of telescoping tubes where the inner tube has a greater length than the outer tube, and the stent surrounds the inner tube, a distal deployment strut fixedly connected at one end to the inner tube, and at the other end non-fixedly connected to the stent, a proximal deployment strut fixedly connected at one end to the outer tube, and at the other end non-fixedly connected to the stent, and an anchoring barb at the distal end of the stent.

As opposed to self-expanding stents, the manually-expandable delivery system of the present invention provides a fixation point for the stent as it is being deployed, to make placement more accurate. Since no balloon is employed, there is nothing to occlude visualization of the vessel lumen during deployment. Furthermore, large diameter stents can be delivered with a small diameter system. The present invention could be used for stent grafting, particularly in large vessels such as the aorta or iliofemoral arteries. Pressure sensitive devices can optionally be added to the delivery mechanism.

Figure 1:
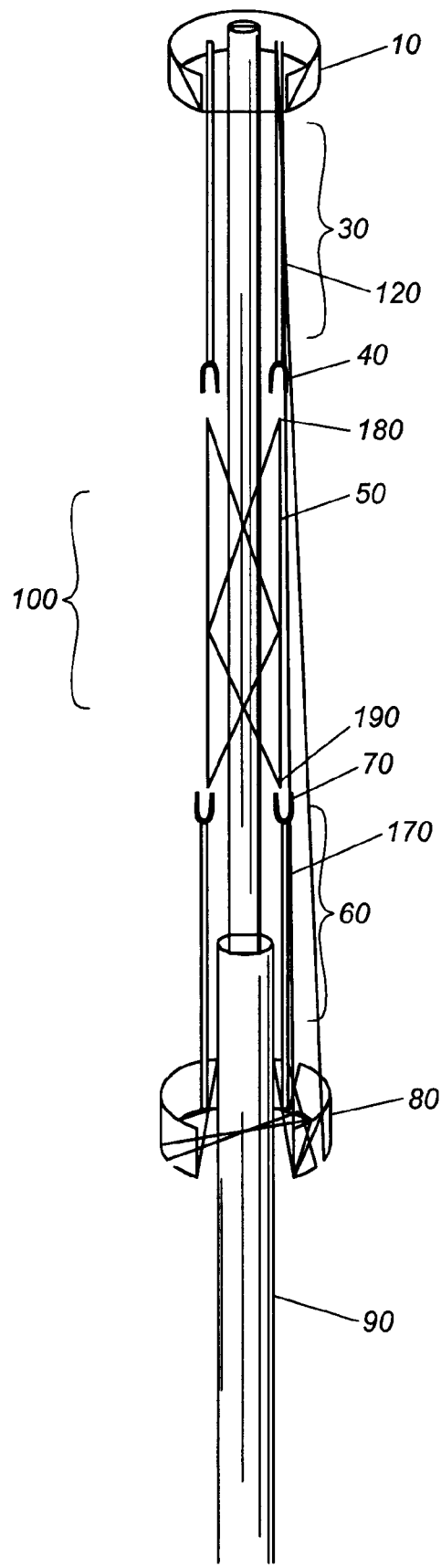
FIG. 1 is a side view of the stent delivery system of the current invention, in elongated form.
Figure 2:
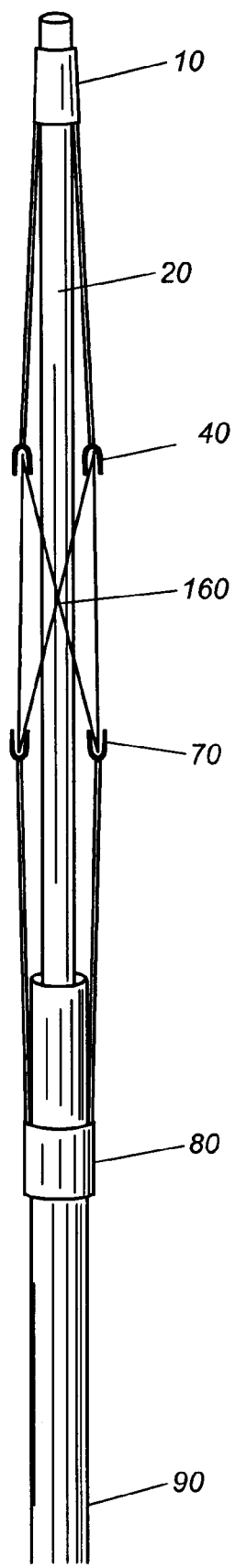
FIG. 2 is a side view of the stent delivery system of the current invention, in elongated form.

FIGS. 1 and 2 show the stent delivery system 100 of the present invention. The outer telescoping tube 90 surrounds an inner telescoping tube 20, and the stent 50 surrounds the portion of the inner telescoping tube 20 that juts out from the outer telescoping tube 90. The distal band 10 secures one end of each distal deployment strut 30 to the end of the inner telescoping tube 20. The U-shaped end 40 of the distal deployment strut 30 fits over the distal rim 180 of the stent. The rod 120 of the distal deployment strut 30 is elastic.

The proximal deployment strut 60 is secured to the outer telescoping tube 90 by means of the proximal band 80. The U-shaped end 70 of the proximal deployment strut 60 fits over the proximal rim 190 of the stent. The rod 170 of the proximal deployment strut 60 is elastic.

Figure 3:
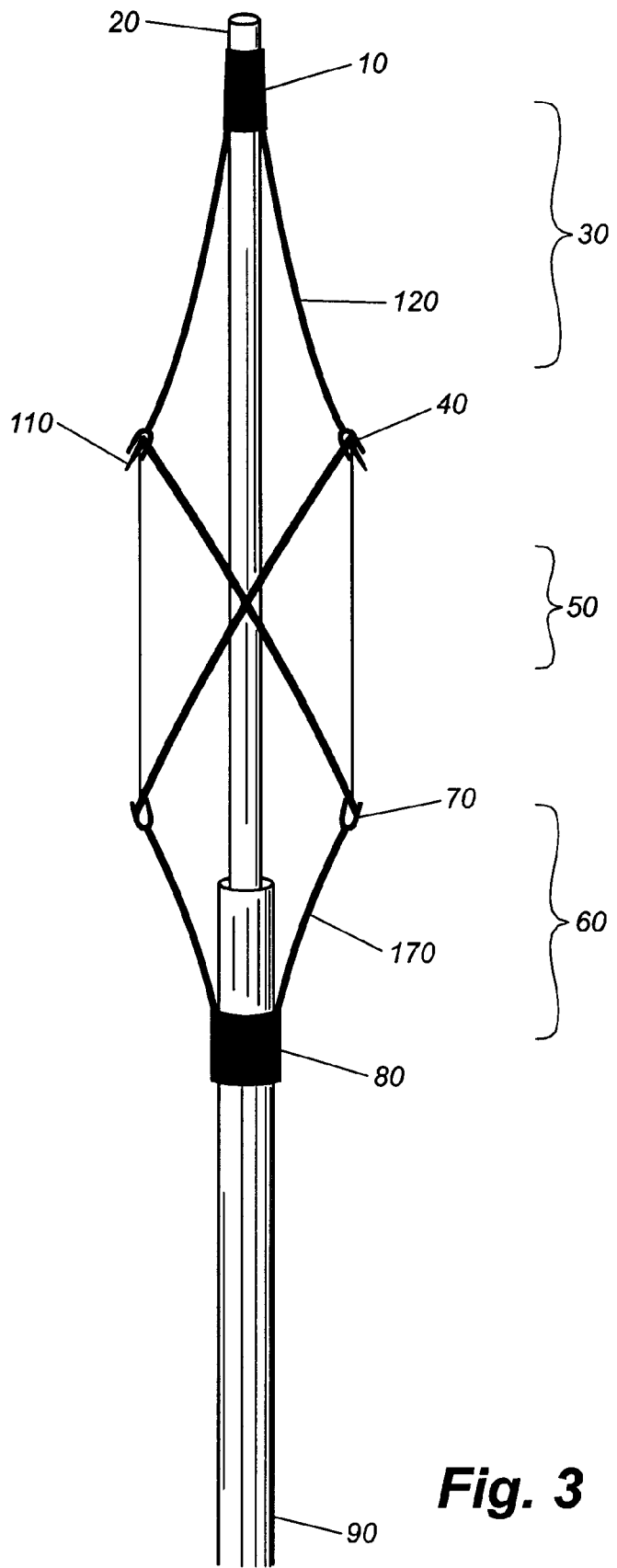
FIG. 3 is a side view of the stent delivery system of the current invention, in compressed form.
Figure 4:
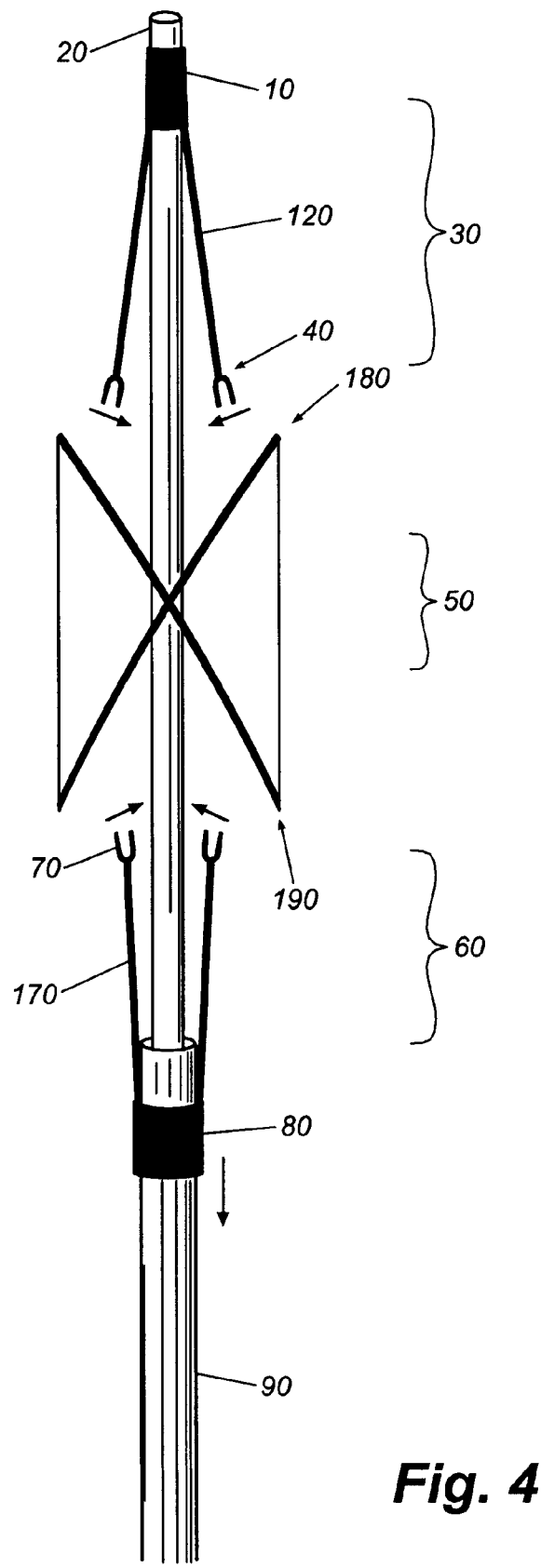
FIG. 4 is a side view of the stent delivery system of the current invention, in compressed form, after both the proximal and the distal struts have released from the stent.
Figure 7A:
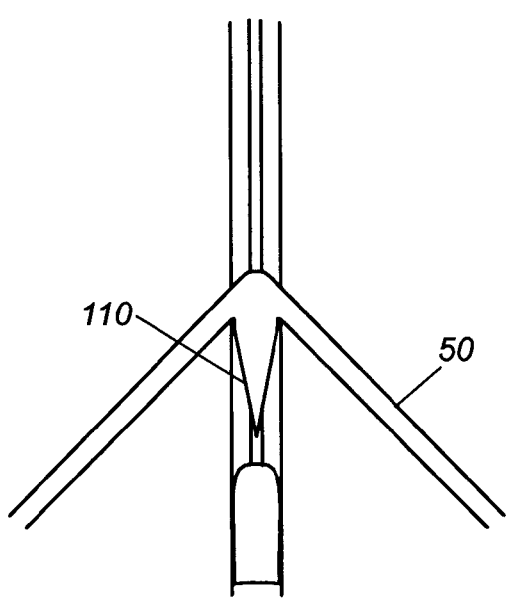
FIG. 7a is an expanded side view of the distal deployment strut of the current invention, after it has released from the distal end of the stent and the anchoring barb, and has moved closer to the inner tube.
Figure 7B:
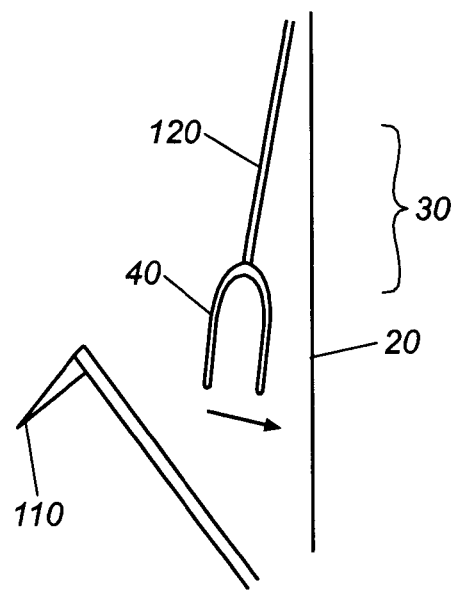
FIG. 7b is an expanded top view of the distal deployment strut of the current invention, after it has released from the distal end of the stent and the anchoring barb, and has moved closer to the inner tube.

FIGS. 3 and 4 show longitudinal compression of the stent. First, the stent delivery system 100 is slid into a desired location in a vessel (not shown). The distal band 10 is moved closer to the proximal band 80 by sliding the outer telescoping tube 90 over the inner telescoping tube 20. This longitudinal compression of the stent 50 causes the girth of the stent 50 to expand. As it expands, as shown by FIGS. 5a, 5b, 6a, 6b, 7a, and 7b, the distal anchoring barb 110 cradled within the distal deployment strut 30 moves outward as well. Eventually, the distal anchoring barb 110 locks within the wall of the vessel (not shown).

The inner telescoping tube 20 is then moved forward, causing the U-shaped end 40 of the distal deployment strut 30 to slide off the distal rim 180 of the stent 50. The elasticity of the rod 120 of the distal deployment strut 30 causes the rod 120 to then lie flat against the inner telescoping tube 20, as shown in FIGS. 4, 6a, 6b, 7a, and 7b. At the same time, the distal anchoring barb 110 becomes fully exposed.

As the outer telescoping tube 90 is moved backwards, the U-shaped end 70 of the proximal deployment strut 60 slides off the proximal rim 190 of the stent 50, as shown in FIG. 4. The elasticity of the rod 170 of the proximal deployment strut 60 causes the rod 170 to then lie flat against both the outer 90 and the inner 20 telescoping tubes.

Figure 9:
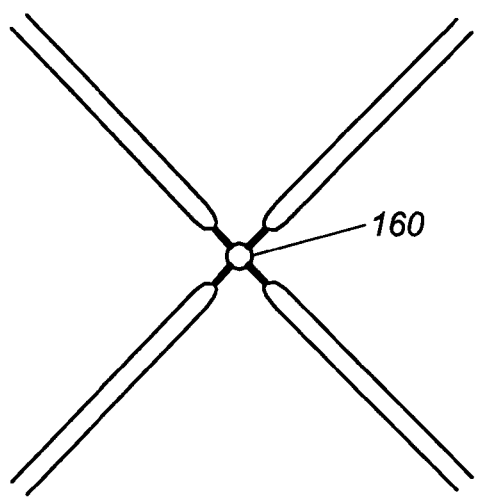
FIG. 9 is a view of a deployment strut which can be used with the present invention.

In one embodiment of the present invention, the longitudinally-compressible stent 50 has stent joints 160 as shown in FIG. 9. In one embodiment, these joints form a diamond pattern, whose individual diamonds become fatter girthwise as they become compressed top to bottom.

Figure 8:
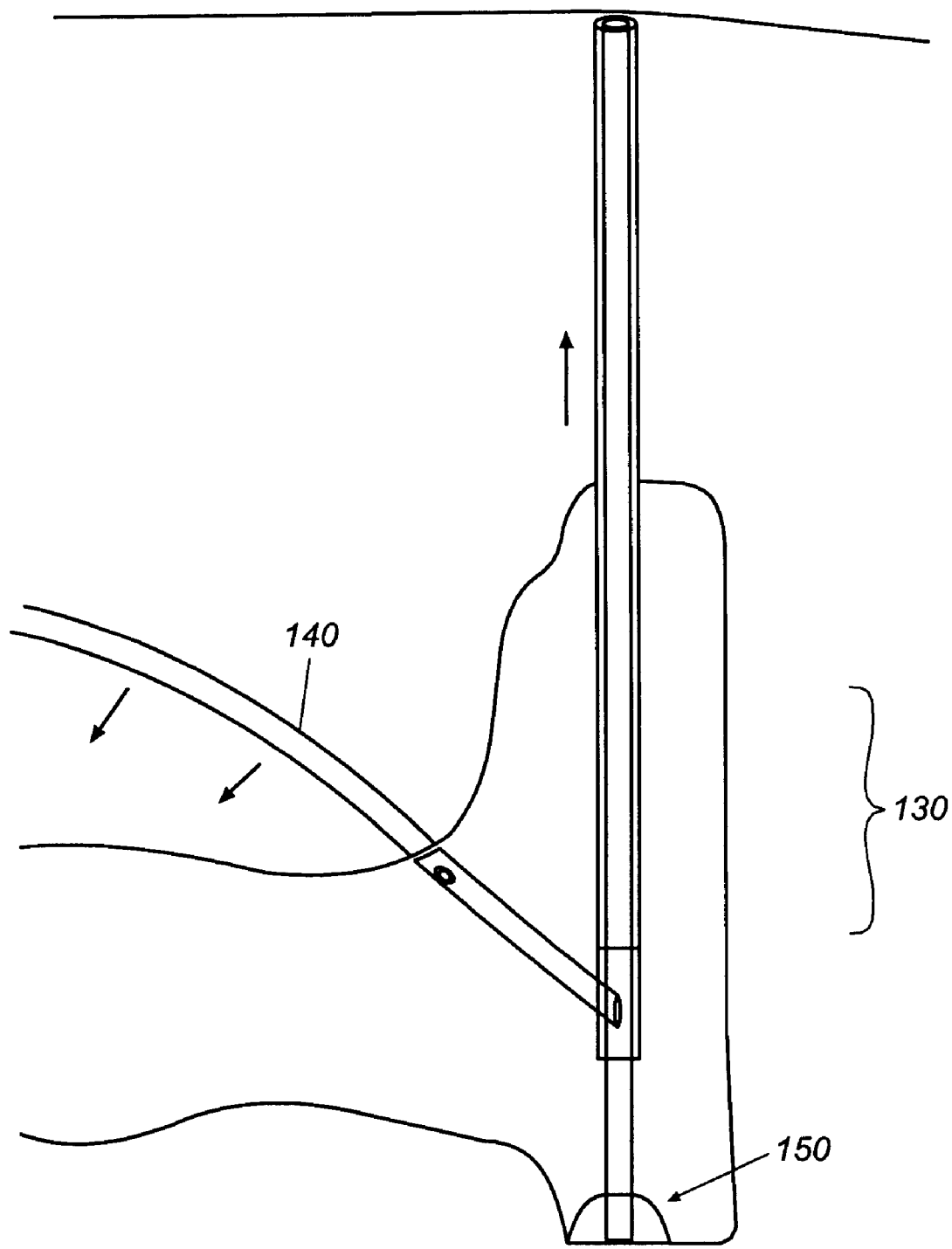
FIG. 8 is a cutaway view of a catheter device which can be used with the present invention.

The stent delivery system 100 of the present invention can be used with the deployment trigger device 130 shown in FIG. 8.

In a another embodiment of the invention, the telescoping tubes 20 and 90 would not telescope, but would be substantially parallel.

Those skilled in the art will now see that certain modifications can be made to the invention herein disclosed with respect to the illustrated embodiments, without departing from the spirit of the instant invention. While the invention has been described with respect to the illustrated embodiments, it will be understood that the invention is adapted to numerous rearrangements, modifications, and alterations, and all of the foregoing are intended to be within the scope of the appended claims.

I claim:

1. A stent delivery system, comprising:
   (a) a stent comprising a proximal end and a distal end and having a girth which expands upon longitudinal compression of the proximal end and distal end;
   (b) a pair of telescoping tubes, wherein the inner tube has a greater length than the outer tube, and the stent surrounds the inner tube;
   (c) a distal deployment strut fixedly connected adjacent one end to the inner tube, and at the other end non-fixedly connected to the stent;
   (d) a proximal deployment strut fixedly connected adjacent one end to the outer tube, and at the other end non-fixedly connected to the stent; and
   (e) an anchoring barb connected to the distal end of the stent.

2. The stent of claim 1, wherein the barb extends outward when the stent is expanded.

3. The system of claim 2, further comprising a plurality of anchoring barbs connected to the distal end of the stent.

4. The system of claim 1, wherein the distal deployment strut cradles the anchoring barb, permitting the barb to extend outward when the stent is expanded.

5. The system of claim 1, wherein the distal deployment strut is non-fixedly connected to the distal end of the stent.

6. The system of claim 2, wherein the proximal deployment strut is non-fixedly connected to the proximal end of the stent.

\* \* \* \* \*